United States Patent [19]
Carson, III et al.

[11] 4,254,179
[45] Mar. 3, 1981

[54] FRAGRANCE IMPREGNATED FOAM AND METHOD OF MAKING THE SAME

[75] Inventors: William S. Carson, III, Woodland, Calif.; Louis A. Carson; Christopher E. Carson, both of Swanton, Ohio; Larry Friedrich, Toledo, Ohio

[73] Assignee: Scottdel, Inc., Swanton, Ohio

[21] Appl. No.: 14,227

[22] Filed: Feb. 22, 1979

[51] Int. Cl.³ .......................... A61K 7/46; C11B 9/00; B01J 13/02; B32B 3/00
[52] U.S. Cl. .................................... 428/311; 252/316; 252/522 A; 252/522 R; 427/294; 427/373; 428/95; 428/315; 428/323; 428/423.1; 428/905
[58] Field of Search ............... 252/522 A, 522 R, 316; 427/294, 180, 373; 428/310, 311, 315, 323, 905, 95, 425, 320, 423.1

[56] References Cited
U.S. PATENT DOCUMENTS

| 2,169,055 | 8/1939 | Overshiner | 252/522 R |
|---|---|---|---|
| 2,911,319 | 11/1959 | Peter | 427/294 X |
| 2,936,814 | 5/1960 | Yakubik | 427/180 X |
| 2,969,330 | 1/1961 | Brynko | 252/316 |
| 3,341,466 | 9/1967 | Brynko | 252/316 |
| 3,495,988 | 2/1970 | Balassa | 252/522 A |
| 3,516,943 | 6/1970 | Brynko et al. | 252/316 |
| 3,565,559 | 2/1971 | Sato et al. | 252/522 A |
| 3,753,922 | 8/1973 | Shimosaka et al. | 252/522 A |
| 3,795,636 | 5/1974 | Huffman et al. | 428/315 X |
| 3,949,742 | 4/1976 | Nowakowsky | 428/315 |
| 4,132,839 | 1/1979 | Marans | 252/522 X |
| 4,145,184 | 3/1979 | Brain et al. | 428/905 X |
| 4,172,917 | 10/1979 | Angelle et al. | 428/315 X |
| 4,188,447 | 2/1980 | Ehlenz | 428/310 |
| 4,193,887 | 3/1980 | Stone et al. | 428/311 X |

Primary Examiner—Harold Ansher
Attorney, Agent, or Firm—Wilson, Fraser, Barker & Clemens

[57] ABSTRACT

A method and apparatus for impregnating a porous foam product with a fragrance which is released over an extended period of time. The method includes the steps of depositing scented particles on one surface of the foam and dispersing the particles within the foam by supplying heat to the foam and applying a vacuum to the opposite surface of the foam. Fragrance or fragrance particles may also be added directly to the foam during its manufacture and a semi-permeable film or fabric may also be affixed to the scented porous foam product to retard and thus extend the release of the fragrance. In a preferred embodiment, frangible encapsulated particles of fragrance are used so that the encapsulated fragrance is retained within the foam until it is later utilized and subject to external forces which break the capsule to release the fragrance.

1 Claim, 3 Drawing Figures

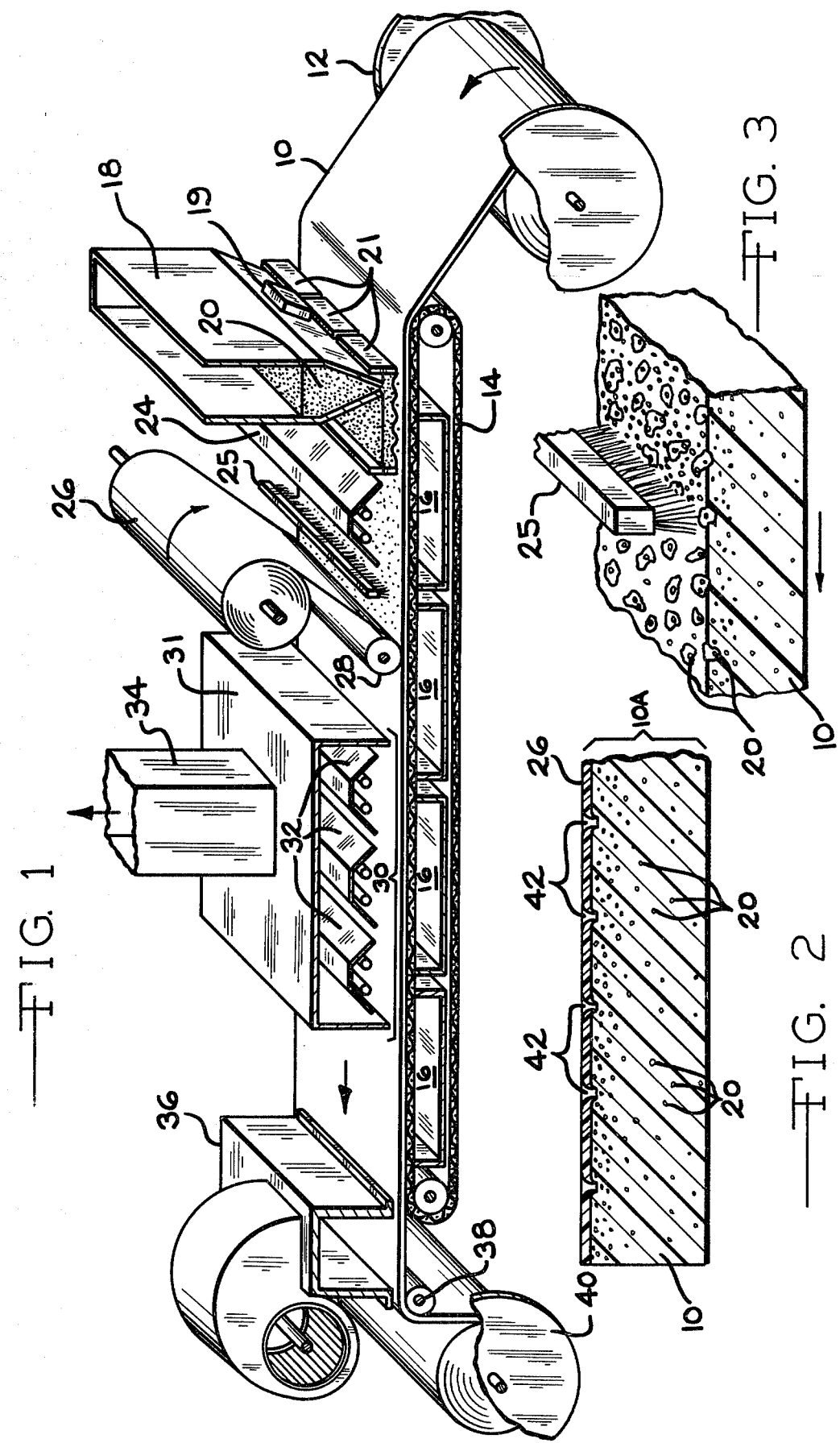

FRAGRANCE IMPREGNATED FOAM AND METHOD OF MAKING THE SAME

BACKGROUND OF THE INVENTION

The invention relates to a method and apparatus for producing scented foam, specifically polyurethane foam or any type of porous foam having fragrance mixed in the foam during manufacture as well as added to the foam in the form of scented particles after it has been cured and cut into a planar sheet.

Polyurethane foams have several characteristics besides easy manufacture and low cost that make them attractive for a number of uses. Good resilience and chemical resistance as well as light weight and good thermal insulating properties have made these foams popular for use as bedding, upholstery, automobile padding and carpet underlay.

One drawback in the use of polyurethane foams is the odor that is released by the foams. Many people find the distinctive odor associated with these foams unpleasant. This odor is particularly objectionable when new carpet and padding is installed due to the large area exposed in a closed interior space. This odor does not dissipate quickly and is often quite detectable for some weeks after installation.

To counteract or overcome the odor released by polyurethane or other synthetic foams having a volatile component which is released over a period of time, a pleasing scent may be added to the porous foam, including foam rubber. The prolonged release of the fragrance in certain products such as cushions is particularly desirable. Heretofore, however, the scents or fragrances added tend to dissipate quickly and then the original objectionable odor becomes dominant throughout the environment.

SUMMARY OF THE INVENTION

The present invention is based upon the discovery that the odor associated with the installation of new carpet and underlay can be overcome by impregnating the padding with a lasting fragrance, either in the form of an encapsulated fragrance which is slowly released as the foam is later used or a slow release fragrance which is long lasting due to the manner in which it is incorporated in the foam. While the invention is useful in masking or overcoming the objectionable odor of foam products of many types, it is described herein as used in the manufacture of foamed carpet padding or underlay.

The foam underlay in the form of a planar sheet is impregnated with a fragrance by application of particles carrying a fragrance to one major surface of the foam sheet. Heat may be applied to the underlay to cause the particles to migrate into the body of the foam. A vacuum is applied to the opposite surface of the foam causing the particles to migrate further into the foam. In addition, mechanical spreading of the particles as by brushing or wiping may be used to distribute the particles across the foam surface and into open voids in that surface. Finally, a semi-pervious layer may be bonded to the foam surface over the particles to retain them in place.

It is a primary object of this invention to provide a fragrance impregnated foam in which the fragrance has a long lasting quality.

It is another object of the invention to provide a method for producing a long lasting fragrance impregnated foam.

Another object of the invention is to provide an apparatus for producing a fragrance impregnated foam.

A further object of the invention is to provide a method and apparatus for producing a fragrance impregnated carpet underlay. Other objects and advantages of the invention will be apparent from the following detailed description of the foam product, the method, and the apparatus of the invention, with reference being made to the accompanying drawings.

BRIEF DESCRIPTION OF THE DRAWINGS

FIG. 1 is a schematic perspective view of the apparatus used to practice the invention;

FIG. 2 is a sectional view of the fragrance impregnated foam, shown on an enlarged scale; and FIG. 3 is an enlarged sectional view in perspective of the fragrance impregnated foam, depicting the function of the spreading device shown in FIG. 1.

DESCRIPTION OF THE PREFERRED EMBODIMENT

Referring to FIG. 1, a planar foam sheet 10, commonly of polyurethane, can be generated from virgin or reprocessed scrap foam. The reprocessed scrap may be molded into a cylindrical log through use of the type of apparatus disclosed in commonly owned U.S. Pat. No. 3,517,414. The log is slit or peeled to form a continuous sheet having a thickness of from ¼ inch to ¾ inch which is rolled upon a supply reel 12 for further handling. Those skilled in the art will appreciate that these foams are highly porous and that the desired degree of porosity for foam used as a carpet underlay is well known to those skilled in the art. Although reference is made to polyurethane foam in the following description, any porous foam that is provided in similar dimensions is suitable for the impregnation of fragrances as described below.

The apparatus for practicing this invention includes the supply reel 12 which holds and supplies the foam sheet 10. An endless conveyor belt 14 is disposed adjacent to and aligned with the supply reel 12. The upper run of the conveyor belt 14 moves away from the supply reel 12 in the direction of the arrows shown, and draws the foam sheet 10 from the supply reel 12 onto the conveyor belt 14. The conveyor belt 14 may be of a fine mesh chain or screen or any flexible foraminous material which permits air to readily pass therethrough. A partial vacuum is maintained in vacuum chambers 16 positioned below the upper run of the conveyor belt 14. The frictional engagement of the foam sheet 10 against the belt 14 due to the partial vacuum is sufficient to draw it from the supply reel 12 and move it with the belt 14.

A hopper 18 is filled with scented particles 20 and extends across the width of the belt 14. A vibrator 19 is secured to the side of the hopper 18 and one or more feed trays 21 are positioned at and secured to the bottom of the hopper 18. The vibrations from vibrator 19 cause the scented particles 20 to be discharged into the feed trays 21 and then dispersed by gravity through the screened bottoms of the feed trays 21 to the upper surface of the foam sheet 10.

The partial vacuum within the chambers 16 and the air drawn through the foam sheet 10 because of the partial vacuum encourages the particles 20 to migrate into the interior of the foam sheet 10. Any of the particles 20 that may travel completely through the foam sheet 10 are drawn into the vacuum chamber 16 and a suction line (not shown) and may be recovered in a suitable collection device (not shown). The recovered particles may then be recycled into the hopper 18.

A heater 24 may be optionally used to supply heat energy to the foam sheet 10 to further assist the migration of the particles 20 into the foam sheet 10. The heater 24 preferably provides heat in the form of radiant energy although forced hot air or other means may be utilized.

In one embodiment of the apparatus, a brush 25 extending the width of the foam sheet 10 sweeps the scented particles 20 remaining on the surface into the open pores of the foam sheet 10. This prepares the surface of the foam sheet 10 to more readily accept any coating. This is schematically illustrated in FIG. 3. A resilient wiper or other device can also be used to spread the particles and wipe clean the surface.

The scented particles 20 which are dispersed in the foam 10 may be frangible microcapsules containing a fragrance. Such microcapsules are available commercially from several sources and are also described in U.S. Pat. Nos. 2,969,330, 3,341,466, 3,516,943 and 3,415,758, which are hereby incorporated by reference.

The use of microcapsules is particularly desirable because release of the scent may be retarded and thus extended over a long period of time. When the frangible microcapsules are subjected to pressure, heat or moisture, the capsules rupture, releasing the fragrance. In this manner release of the fragrance may be prolonged over an extended period of time. Handling of the carpet during installation will fracture some of the microcapsules thus liberating the fragrance. After the carpet has been installed and the initial scent has dissipated, the fragrance will continue to be released whenever the microcapsules are subjected to changes in presure, moisture or heat. For example, merely walking across the carpet will result in liberation of the fragrance, as the pressure ruptures some of the microcapsules. The composition and thickness of the microcapsule coating may be adjusted to provide the desired fragrance release based upon anticipated factors such as maximum temperature and pressure. Alternatively, the scented particles 20 may be composed of bone material, clay or charcoal that have been treated with a fragrance. Such particles do not, of course, exhibit such a prolonged fragrance release characteristics of the microcapsules. Their utilization does, however, produce a foam product having a fragrance release time substantially longer than that exhibited by a foam which has had fragrance added directly to it during its manufacture. This delay is a result of the slow adsorption properties of materials such as bone material, clay and charcoal. Fragrance that has been added to these carriers is released slowly to the surrounding atmosphere, thereby producing a time delay effect in the release. The scented particles 20 are generally 200 mesh or finer to facilitate the dispersing from the hopper onto the foam. Experiments on possible carriers for the fragrance show Attapulgus clay, Western Bentonite and Southern Bentonite as excellent carriers.

To increase the amount of scent imparted to the foam underlay, the fragrance may be added to the porous foam during manufacture of the log. The fragrance may be imparted to the foam by adding microcapsules containing the fragrance or particles carrying the fragrance or the fragrance itself to the virgin batch or the reprocessed batch. If microcapsules are added during the manufacture of the log, most of the capsules will rupture due to the heat and pressure created in the processing. Therefore, much of the fragrance is immediately liberated.

It is often desirable to laminate the carpet underlay to reduce the friction between the carpet and the underlay as well as to add tear resistance. A porous laminate has the added advantage of eliminating trapped water vapor and condensation. The fragrance impregnated foam may be laminated with a film or fabric permeable to the fragrance molecules. The film or fabric should be porous in the sense that the structure of the film allows the fragrance molecule to escape, and should have a low coefficient of friction. FIG. 2 illustrates such a structure. The porosity of the film is such that it will pass entrained water vapor but yet is less permeable than the foam itself so that a fairly unbroken and smooth upper surface is presented to the underside of the carpet above. The film may be laminated as follows.

A laminated foam sheet 10A (FIG. 2) may be produced by feeding an impervious plastic film 26 to the surface of the foam sheet 10 under a roller 28 which presses the film 26 onto the foam 10. The vacuum chambers 16 below the conveyor belt 14 draw air downwardly through the belt to apply sufficient vacuum to hold the plastic film 26 against the foam sheet 10 before, during and after passage of the foam 10 and the film 26 through a heating zone 30. The heating zone 30 is defined by an overhead hood 31 which covers the conveyor belt 14 completely with the lower edges of the hood 31 closely approaching the conveyor belt 14 to confine the heat generally within the hood 31. A bank of heaters 32 which may be identical or similar to the heater 24 supply heat, preferably in the form of radiant energy to the film 26 and the foam sheet 10. The temperature in the heating zone 30 should preferably be maintained below the temperature at which the coating of the microcapsules 20 deteriorates. A conventional exhaust system 34 carries excess heat from the heating zone 30. A cooling air source 36 is used to cool the porous laminated foam sheet 10A as it exits the heating zone 30. A guide roller 38 directs the laminated foam sheet 10A onto a winding reel 40 where it is collected.

Thermoplastic films such as polyethylene or copolymers of ethylene and acrylic acid, methacrylic acid and crotonic acid may be used. As the foam sheet 10 and plastic film 26 are subjected to heat in the heating zone 30, the film 26 becomes tacky and adheres to the foam 10. Additional heat causes the film 26 to shrink and form small voids, thus developing the desired porosity in the film.

Referring now to FIG. 2, the sheet 10A comprises the foam sheet 10 having scented particles 20 dispersed therein and the plastic film 26 on one surface. The plastic film 26 defines pores or voids 42 which permit the fragrance molecules to escape from the upper surface of the foam sheet 10. As schematically illustrated, the number of voids 42 in the film 26 are relatively widely scattered over the film surface so that the fragrance or essence particles are partially covered by the semi-porous film 26 and therefore the film itself impedes the release of the desirable odor. This is in addition to the delay which is caused by encapsulation of the fragrance particle.

It will be seen from the above description that the instant invention provides a foam structure particularly suited for a carpet underlay in which a desirable odor is slowly released over a relatively long period. The delayed release may be caused by the fact that the fragrance particles are (1) encapsulated and later broken by use, (2) are mixed with a carrier having adsorption characteristics which prolong the beneficial effects of the fragrance or (3) partially shielded or covered by the semi-pervious laminated sheet which delays the release of the fragrance to the atmosphere. In some constructions, it may be desirable to combine two or more of these effects with fragrance particles which are not encapsulated or mixed with a carrier so that the resulting product has a fast release of fragrance followed by the prolonged release thereof. Thus, depending upon the nature of the end use of the product, the fragrance addition can be programmed or adjusted to the optimum results.

Various other advantages and modifications of the above described preferred embodiments will be apparent to those skilled in the art and may be made without departing from the spirit and scope of the attached claims.

We claim:

1. A fragrance impregnated foam comprising a generally planar body of porous foam having an upper surface containing open voids, a plurality of frangible microcapsules containing a fragrance positioned within such voids, and a semi-pervious film adhered to said upper surface covering said open voids and said microcapsules therein, whereby the fragrance of said particles migrates through and is liberated from said plastic film over an extended period of time.

* * * * *